United States Patent [19]
Howard

[11] Patent Number: 5,363,857
[45] Date of Patent: Nov. 15, 1994

[54] METABOLIC ANALYZER

[75] Inventor: Charles P. Howard, Ann Arbor, Mich.

[73] Assignee: AeroSport, Inc., Ann Arbor, Mich.

[21] Appl. No.: 69,513

[22] Filed: Jun. 1, 1993

Related U.S. Application Data

[60] Continuation-in-part of Ser. No. 20,663, Feb. 22, 1993, which is a continuation of Ser. No. 751,550, Aug. 29, 1992, abandoned, which is a division of Ser. No. 527,106, May 22, 1990, Pat. No. 5,060,656.

[51] Int. Cl.$^5$ .............................................. A61B 5/08
[52] U.S. Cl. .................................... 128/718; 128/719
[58] Field of Search .............. 128/716, 718, 719, 622, 128/205.22, 205.23; 356/41

[56] References Cited

U.S. PATENT DOCUMENTS

| | | |
|---|---|---|
| 2,787,999 | 4/1957 | Bennett . |
| 3,035,569 | 5/1962 | Dubsky et al. . |
| 3,250,270 | 5/1966 | Bloom . |
| 3,401,683 | 9/1968 | Webb et al. . |
| 3,754,815 | 8/1973 | Sanctuary et al. . |
| 3,799,149 | 3/1974 | Rummel et al. . |
| 3,818,901 | 6/1974 | Sanctuary et al. . |
| 3,895,630 | 7/1975 | Bachman . |
| 3,989,037 | 11/1976 | Franetzki . |
| 4,006,634 | 2/1977 | Billette et al. . |
| 4,197,857 | 4/1980 | Osborn ............................ 128/718 |
| 4,297,871 | 11/1981 | Wright et al. . |
| 4,363,238 | 12/1982 | Willam . |
| 4,368,740 | 1/1983 | Binder . |
| 4,372,169 | 2/1983 | Hughes . |
| 4,403,514 | 9/1983 | Osborn . |
| 4,546,778 | 10/1985 | Sullivan . |
| 4,572,208 | 2/1986 | Cutler et al. . |
| 4,619,269 | 10/1986 | Cutler et al. . |
| 4,649,027 | 3/1987 | Talbot . |
| 4,765,326 | 8/1988 | Pieper . |
| 4,915,132 | 4/1990 | Hodge et al. ................. 128/205.24 |
| 4,928,703 | 5/1990 | Wong .............................. 128/719 |
| 4,968,137 | 11/1990 | Yount .............................. 123/633 |
| 5,038,773 | 8/1991 | Norlien et al. . |
| 5,069,220 | 12/1991 | Casparie et al. ................ 128/719 |

Primary Examiner—Lee S. Cohen
Assistant Examiner—Robert L. Nasser
Attorney, Agent, or Firm—Michael A. Mohr

[57] ABSTRACT

A metabolic rate analyzer is provided comprising a $CO_2$ detector, an $O_2$ detector, a flow resistance, a differential pressure transducer, a solenoid-actuated metering valve for producing a volumetrically-proportional sample of respired gas, a vacuum regulator for receiving the sample, a pump for drawing the sample from the vacuum regulator, and a processor for periodically sampling the differential pressure signal to provide a flow signal, to modulate power applied to the solenoid-actuated flow proportioning valve, and to provide a measure of the total volume of respired gas. The processor correlates the total volume of respired gas, $O_2$ content and $CO_2$ content to provide a measure of metabolic rate. Flow is recycled between the pump and the regulator valve to provide a source of mixed respired gas for analysis and digital integration of the flow signal provides a measure of the total volume of respired gas. A pulse generator driven by the microprocessor varies the frequency of pulses applied to the metering valve and the pulse width to provide volumetrically-proportional sampling and to control the effective sample volume of the analyzer, respectively. The processor determines the slope of the flow signal and increases the periodic sample rate of the pressure signal when slope is increasing and decreases the periodic sample rate when slope is decreasing to provide derivative augmentation of the sample period.

32 Claims, 7 Drawing Sheets

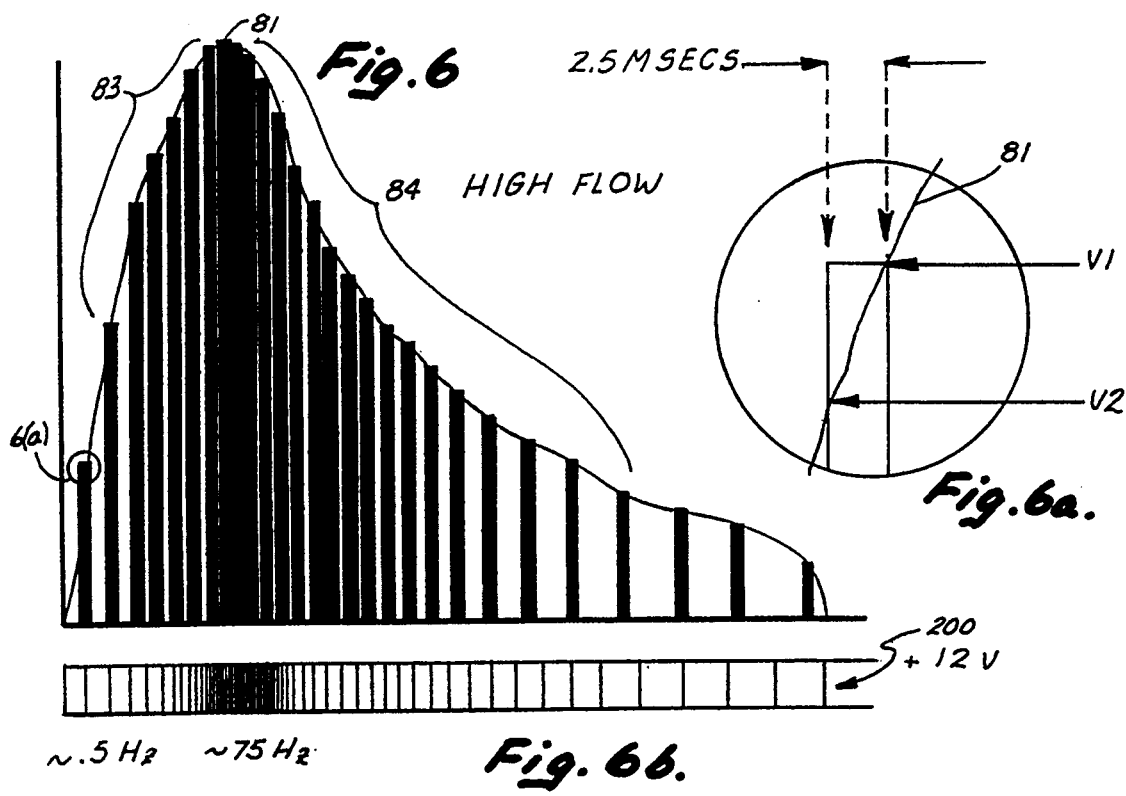
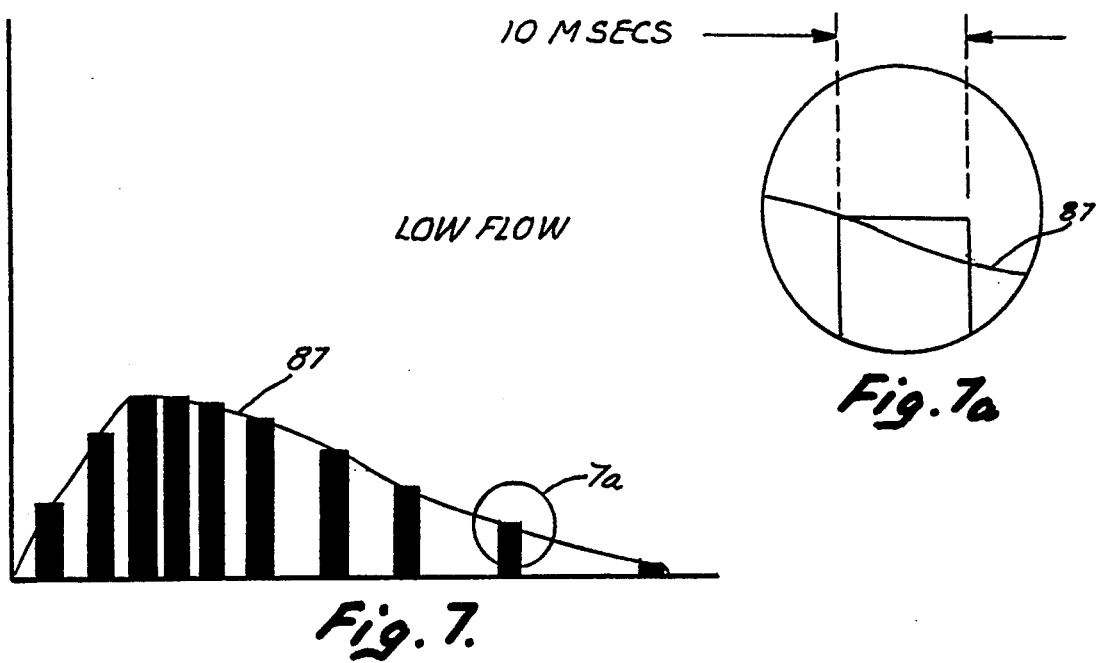

METABOLIC ANALYZER

RELATED CASES

This is a continuation-in-part of co-pending application Ser. No. 08/020,663, filed on Feb. 22, 1993, of Charles P. Howard, for METABOLIC RATE ANALYZER, which is a continuation of abandoned application Ser. No. 07/751,550, filed on Aug. 29, 1992, of Charles P. Howard, for METABOLIC RATE ANALYZER, which is a divisional application of U.S. Pat. No. 5,060,656, Application Ser. No. 07/527,106, filed on May 22, 1990, of Charles P. Howard, for METABOLIC RATE ANALYZER; and is related to U.S. Pat. No. 5,117,674, filed Aug. 290, 1991, of Charles P. Howard, for METABOLIC RATE ANALYZER. The disclosure of prior U.S. Pat. No. 5,060,656, noted above, is hereby incorporated by reference.

BACKGROUND OF THE INVENTION

1. Field Of The Invention

The invention relates generally to the art of gas analysis and, more particularly, is directed to a new metabolic rate analyzer.

2. Description Of The Related Art

All of the processes that take place in the body ultimately result in the production of heat. Heat production and metabolism can be viewed in a similar context. In direct calorimetry heat production is measured directly to provide a measure of metabolic rate or function.

All energy metabolism in the body ultimately depends on the utilization of oxygen. Indirect calorimetry involves measuring the consumption of oxygen ($O_2$) and the production of carbon dioxide ($CO_2$) to provide an indirect estimate of energy metabolism. There are many different gas analysis techniques used in the prior art of indirect calorimetry. These gas analysis techniques are used by physicians for clinical reasons, by athletes to measure performance, and by coaches to measure fitness levels.

It has been known for some time that the analysis of a subject's respired air provides valuable information relating to the physical condition of the subject. The four most commonly measured variables are respiratory volume, oxygen consumption, carbon dioxide production, and respiratory exchange ratio (RQ), which is the ratio of carbon dioxide produced to oxygen consumed.

One of the earliest efforts to conduct indirect metabolic rate analysis involved use of a so-called Douglas Bag. A Douglas Bag metabolic analysis technique involved the timed collection of expired breath in a rubberized bag, measuring the volume of expired gas collected, and analyzing the gas composition contained within the rubberized bag for $O_2$ and $CO_2$ content. Metabolic rates were then calculated from the data obtained. The Douglas Bag technique was time consuming, subject to error, and could only be performed on relatively stationary subjects in well-equipped laboratories. Also, this technique was not well-suited to the measurement of short-duration transients in metabolic functions.

Since the data obtained from respiratory gas analysis is so valuable in diagnosing cardiopulmonary dysfunction and evaluating overall cardiovascular fitness, intense effort has been directed towards the development of simpler, faster, automated metabolic analyzers. The intense interest in physical fitness and aerobic exercise, such as running, as helped to focus further effort in this field. Many instruments are presently available for the determination of the total volume of respired air from a subject being studied. These devices include spirometers, plethysmographs, and pneumotachographs. Numerous instruments are also available for determining $O_2$ content and $CO_2$ content in respired gas. Some of the more recent techniques involved the use of a discrete zirconium oxide $O_2$ sensor and a non-dispersive infrared (NDIR) gas analyzer for determining $CO_2$ content. While, such instruments are accurate, they are large, heavy, they require frequent calibration, and special operating skills. Normally, such instruments are so large that they are incorporated in a wheeled cart, which is used only in a clinical or laboratory setting.

SUMMARY OF THE INVENTION

According to the present invention, these and other problems in the prior art are solved by provision of a metabolic rate analyzer comprising a $CO_2$ detector for determining the $CO_2$ content of a respired gas, an $O_2$ detector for determining the 02 content of the respired gas, a flow restriction through which the respired gas is directed, a differential pressure detector connected to the flow restriction for providing a differential pressure signal representative of the flow of respired gas through the flow restriction, a solenoid-actuated metering or flow proportioning valve connected to a source of respired gas for delivering a volumetrically-proportional sample of respired gas, a vacuum regulator for receiving the sample, a pump for drawing the sample from the vacuum regulator and delivering a sample of respired gas to the $CO_2$ and $O_2$ detectors, and a processor for converting the differential pressure signal into a flow signal that is representative of the volumetric flow of the respired gas that established the differential pressure signal. The processor uses the flow signal to modulate electrical power applied to the solenoid-actuated metering valve to provide a sample of respired gas having a known volumetric relationship with the total volume of respired gas. The processor then determines the total volume of respired gas and correlates total respired gas volume, $CO_2$ content and $O_2$ content to provide a measure of metabolic rate.

According to other aspects of the invention, the pump is provided with first and second outputs. The first output of the pump is directed back to the regulator to provide a loop flow of mixed respired gas. The second output of the pump is directed to the $CO_2$ detector and the $O_2$ detector for delivering a sample of mixed respired gas thereto. A pulse generator is provided having a variable frequency and a variable pulse width output, which are controlled by the processor and a flow signal derived from the differential pressure signal. The frequency of the output of the pulse generator is increased with an increase in the flow signal, and decreased with a decrease in the flow signal. The output of the pulse generator is applied to the actuating coil of the solenoid-actuated metering valve to produce a volumetrically-proportional sample. The processor integrates the flow signal to provide a measure of the total volume of respired gas. The processor monitors the flow signal to determine breath rate and controls the pulse width of the output of the pulse generator. Pulse width is increased when breath rate is low and decreased when breath rate is high to control the effective sample volume of the analyzer. The processor has a variable period for sampling the pressure signal, and the processor determines the slope of the flow signal for increasing the period when the slope is decreasing and increasing the period when the slope is decreasing, thus effecting a derivative augmentation of the sampling period.

According to other aspects of the present invention, a single beam NDIR gas analyzer is used to conduct $CO_2$ analysis, which features an automatic calibration technique. More particularly, a body having a known absorption for infrared energy corresponding to a specific $CO_2$ gas content is mounted for reciprocal motion in the optical path between the infrared (IR) source and IR detector. During the automatic calibration of the metabolic rate analyzer of the present invention, ambient air is drawn into the system to span the oxygen detector and the reciprocal body is displaced into the optical path of the NDIR $CO_2$ analyzer to automatically calibrate the analyzer without the need to reference a calibration gas, a reference cell, or the like.

BRIEF DESCRIPTION OF THE DRAWINGS

FIG. 6 is a plot of flow versus time for high flow and high breathing rate conditions;

FIG. 6(a) is an enlarged view of FIG. 6, illustrated derivative augmentation and a narrow pulse width associated with the high flow and high breathing rate conditions of FIG. 6;

FIG. 6(b) is a plot of a digital frequency-proportional flow signal that drives the solenoid-actuated metering valve.

FIG. 7 is a plot of flow versus time for low flow and low breathing rate (basil) conditions, illustrating derivative augmentation and pulse width modulation to accommodate for low flow rates;

FIG. 7(a) is an enlarged view of a portion of the plot of FIG. 7 to illustrated derivative augmentation and the wider pulse rates used in basil flow conditions to increase the effective sample volume of the metabolic rate analyzer;

DESCRIPTION OF THE PREFERRED EMBODIMENTS

Figure 1:
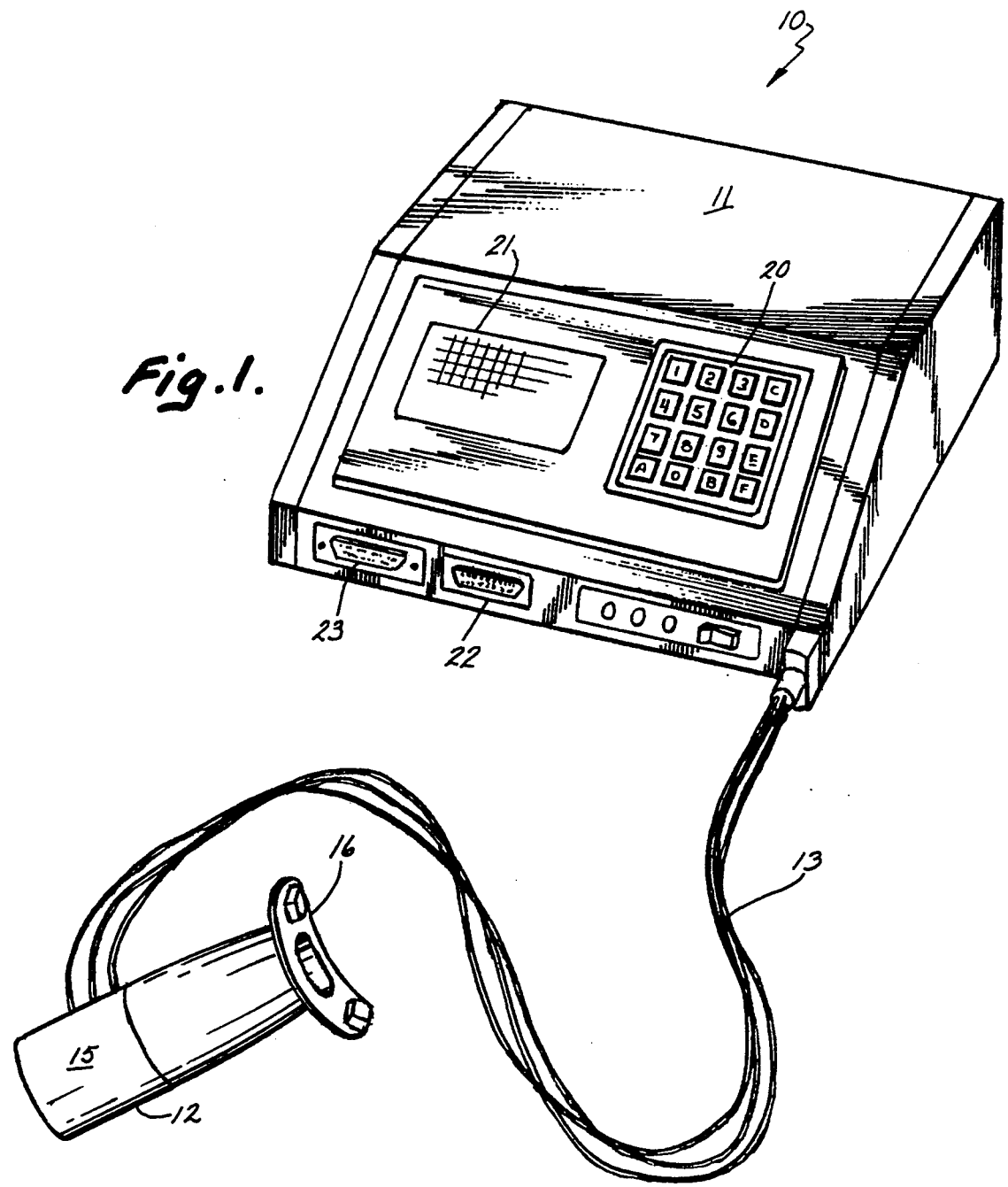
FIG. 1 is a perspective view of the metabolic rate analyzer of the present invention.

With reference now to the Figures, and in particular FIG. 1, the metabolic rate analyzer of the present invention is generally illustrated at 10. In the preferred embodiment, the analyzer comprises a console 11, a flow detector 12, and a plurality of pressure and/or sampling tubes 13 interconnecting the console 11 and the flow detector 12. The flow detector 12 comprises a generally cylindrical body 15 having an elastomeric mouthpiece 16 which is held in the user's mouth. A noseclamp not illustrated herein is normally placed over the user's nose to ensure that all of the user's respired gas is discharged through the mouthpiece 16. The console 11 is small and portable. The console is suitable for transport by hand. Further miniaturization of components is possible, but in this preferred embodiment, total weight is about seven pounds, including an internal rechargeable battery power source, and the footprint of the console 11 is less than one square foot. This represents a remarkable reduction in the size, weight, and ultimate cost, of metabolic rate analyzers, since conventional metabolic rate analyzers are generally suitable for institutional or clinical use, and are often built into wheeled carts which are not suitable for hand transport.

The console further includes a keyboard 20, a liquid crystal display 21, an RS232 port at 22 for interfacing with an external computer, and a printer port 23 for driving an external printer during long metabolic studies.

Figure 2:
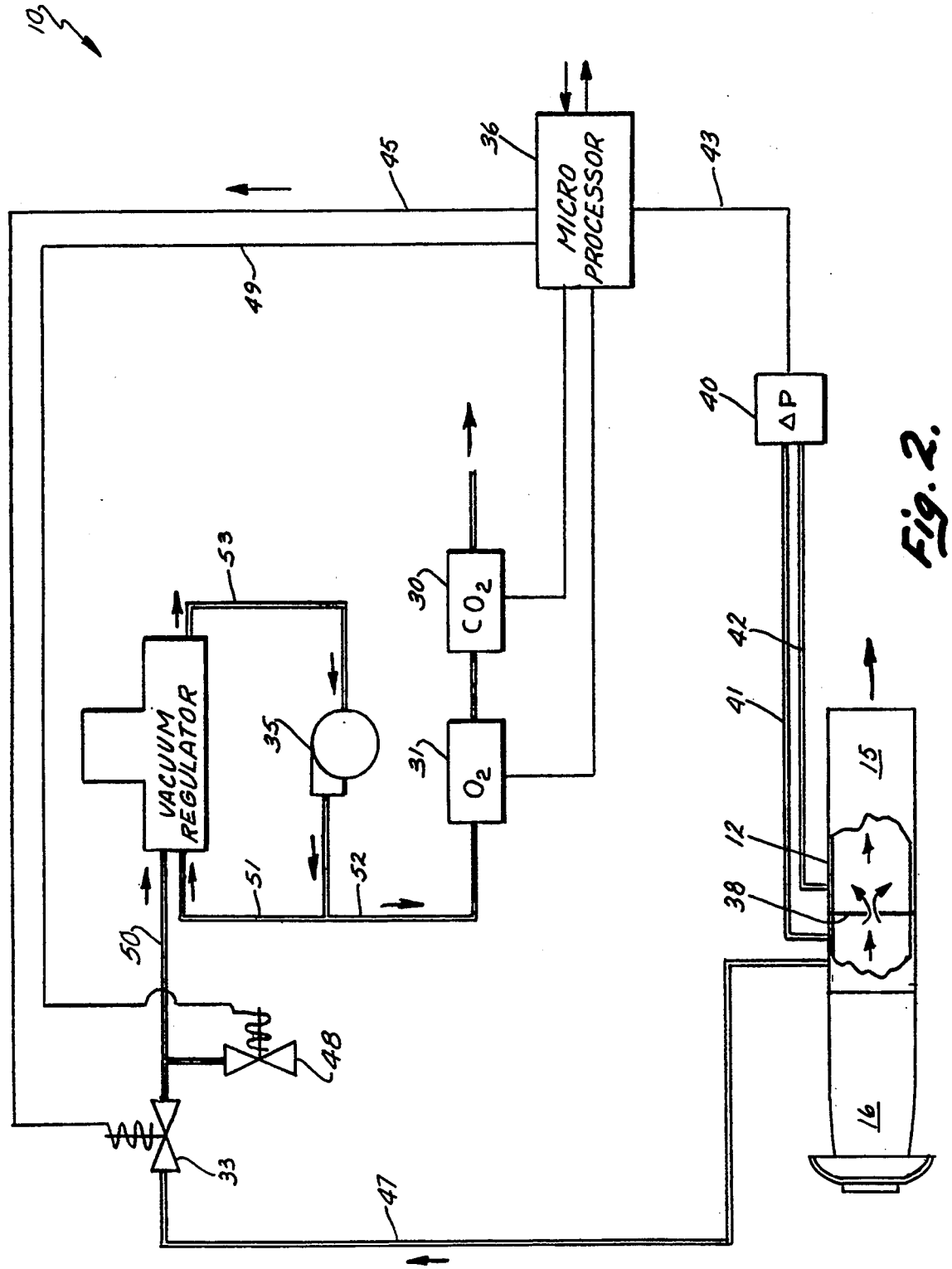
FIG. 2 is a functional diagram of the metabolic analyzer of the present invention.

With reference now to FIG. 2, the metabolic rate analyzer of the present invention is schematically illustrated. The analyzer comprises a $CO_2$ detector at 30. In the preferred embodiment, the $CO_2$ detector is a single-beam, non-dispersive, infrared (NDIR) gas analyzer, which is hereinafter described. Such NDIR $CO_2$ detectors are known in the art, and the detector used in this preferred embodiment is commercially available from DynaTech Electro Optics of Saline, Mich. An $O_2$ detector is disposed at 31. The $O_2$ detector is preferably a galvanic cell-type. The $O_2$ detector of this preferred embodiment is commercially available from City Technology Ltd., a U.K. corporation. The flow detector of the present invention is illustrated at 12. A solenoid-operated metering or flow proportioning valve is disposed at 33 for delivering a measured sample of respired gas from the mouthpiece 16 of the flow detector 12. A vacuum regulator is disposed at 34 for receiving the sample of respired gas. A pump at 35 draws the sample of respired gas from the vacuum regulator and delivers the sample to the $CO_2$ and $O_2$ detectors 30 and 31. A microprocessor at 36 converts a differential pressure signal derived from the flow detector 12 into a sampling signal that is applied to the metering valve 33 to provide a sample of respired gas having a known volumetric relationship with the total volume of respired gas passing through the flow detector 12. The processor determines the total volume of respired gas and then correlates total volume, $CO_2$ content, and $O_2$ content to provide a measure of metabolic rate.

Figure 3:
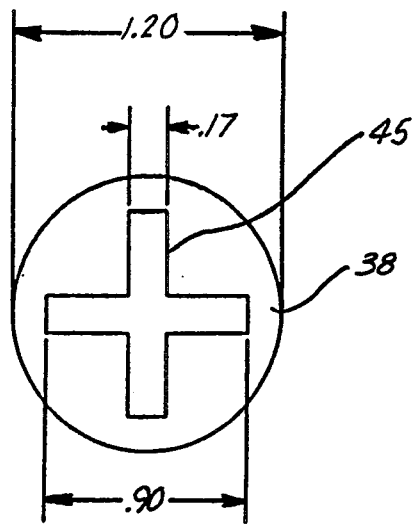
FIG. 3 is a plan view of an orifice plate in the flow detector of the metabolic rate analyzer.

With continued reference to FIG. 2, the flow detector 12 of the present invention includes a flow restriction 38 in the form of an orifice plate which provides a restriction to the flow of respired gas. A typical orifice plate 38 is illustrated in further detail in FIG. 3 with nominal dimensions illustrated directly thereon in inches. The orifice plate 38 is formed from a sheet of stainless steel 0.005 inch thick. The dimensions for the orifice plate 38 illustrated in FIG. 3 are optimized for the study of an adult human subject. A differential pressure transducer at 40 in FIG. 2 senses the pressure drop across or on opposing sides of the orifice plate 38 via flexible tubes 41 and 42. The differential pressure transducer 40 thus provides a signal that is representative of the pressure drop across the orifice plate 38. This differential pressure signal has a known relationship to the flow of respired gases passing through the orifice plate 38.

In this preferred embodiment, an orifice plate 38 is provided which comprises a sharp plate orifice. The flow characteristics of a sharp plate orifice are known in the art. While other flow restrictions having a known relationship such as those associated with a flow nozzle or a venturi could be used, the sharp plate orifice is preferred. A sharp plate orifice produces a differential pressure signal, which is proportional to the square of the flow of respired gas in the flow detector 12. The microprocessor 36 provides a flow signal which is representative of the flow of respired gas through the flow detector 12 by taking the square root of the differential pressure signal. The differential pressure signal is inputted to the microprocessor 36 via line 43 and an analog-to-digital (A/D) convertor, not illustrated in FIG. 2. With reference now again to FIG. 3, it is illustrated that the orifice plate 38 is provided with an orifice 45 having a cross shape, which reduces the flow resistance through the flow detector 12 while still providing performance comparable to a classic sharp plate orifice.

The microprocessor 36 controls the output of a pulse generator or valve driver circuit, not illustrated in FIG. 2, which sends a pulse train on line 45 to solenoid-actuated metering or flow proportioning valve 33. The power applied to the solenoid-actuated metering valve 33 is proportional to the flow signal calculated by the microprocessor so that a small but representative sample of the respired gas having a known volumetric relationship with the total volume of respired gas discharged through the mouthpiece is drawn through the metering valve 33 on line 47. The solenoid-actuated metering valve 33 is normally closed and a second solenoid-actuated valve 48 is opened by the microprocessor 36 via line 49 only when ambient air is to be introduced into the system to span and/or calibrate the $O_2$ and $CO_2$ sensors during the start-up of the metabolic rate analyzer.

The pump 35 is provided with a first output on line 51 and a second output on line 52. The first output of the pump 35 on line 51 is directed back to the vacuum regulator 34 to provide a loop of mixed respired gas circulating through the vacuum regulator 34 and the pump 35. The second output 52 of the pump 35 is directed to the $O_2$ and $CO_2$ analyzers 31 and 30, respectively, to deliver a sample of mixed respired gas when pulses issuing from the microprocessor 36 actuate the solenoid-actuated metering valve 33 to admit sample gas to the vacuum regulator 34, altering the flow balance in the closed loop represented by lines 53 and 51, extending between the vacuum regulator 34 and the pump 35. The output of the vacuum regulator 34 on line 53 is normally held to a constant vacuum, in this case approximately five inches of mercury. When the metering valve 33 is closed, flow from the pump 35 is discharged through the second output 52 until the preset output value of the vacuum regulator 34 is reached. Thus, a closed loop flow of mixed respired gas is established until the metering valve 33 is opened, admitting additional sample gas to the loop and resulting in a corresponding discharge of mixed respired air through the line 52 to the $O_2$ and $CO_2$ detectors.

Figure 4:
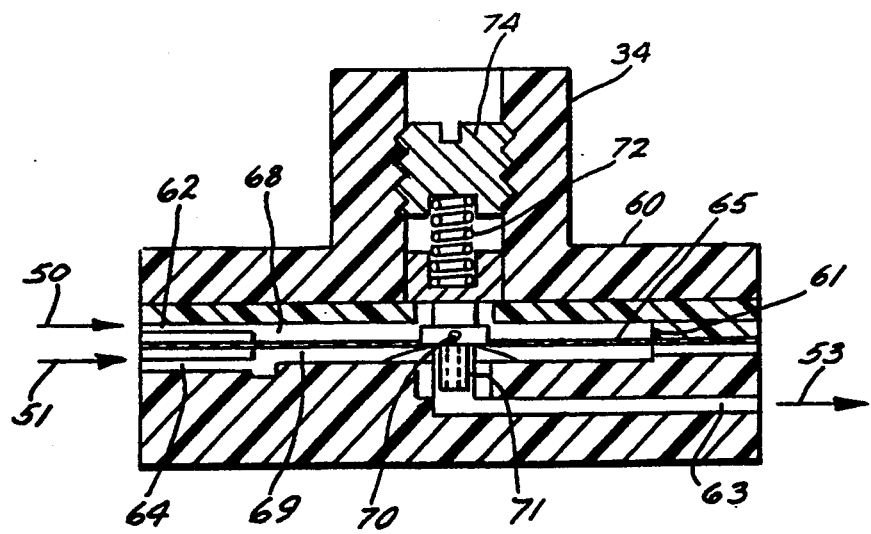
FIG. 4 is an elevational view, partially in section, of a vacuum regulator of the metabolic rate analyzer.

With reference now also to FIG. 4, the vacuum regulator 34 of the present invention is illustrated in further detail. The vacuum regulator 34 comprises a regulator body 60 which defines a gas chamber at 61. A regulator input port is disposed at 62. The input port receives the flow from line 50 to connect the output of the metering valve 33 to the regulator 34. A regulator output port is disposed at 63 for delivering sample gas at a predetermined vacuum to line 53 and the input of the pump 35. A recycle port is disposed at 64 for receiving the first output of the pump 35 on line 51. A flexible diaphragm 65 is disposed between the regulator input port 62 and the regulator output port 63 for dividing the gas chamber 61 into an input side 68 and an output side 69 in fluid communication with the regulator input port 62 and the regulator output port 63, respectively. A metering port 70 is disposed in the diaphragm 65 for establishing a fluid communication between the input side 68 and the output side 69 of the gas chamber. A transfer port 71 is disposed in a seat disposed in the output side 69 of the gas chamber. The diaphragm 65 is spring biased by compression-loaded coil spring 72 into engagement with the transfer port 71 to keep the transfer port normally closed except for the metering port 70 which extends therethrough. A set screw 74 adjusts the spring bias of compression-loaded coil spring 72 to adjust the sealing force of the diaphragm 65 against the seat containing transfer port 71.

As heretofore described, the vacuum regulator 34 holds the output on line 53 at a known vacuum, which is established by the pressure of the coil spring 72 against flexible diaphragm 65. Flow is discharged through the second output 52 of the pump 35, illustrated in FIG. 2, until the predetermined vacuum setpoint of the output of the regulator 34 is reached. The flow balance within the closed loop, including regulator output port 63, pump 35, and regulator recycle port 51 is disturbed when the metering valve 33 admits additional sample gas into the input side 68 of the gas chamber 65. The additional sample gas is metered through the metering port 70 and is discharged through the regulator output port 63 to add to the flow in line 53 entering pump 35. This increases the pressure on the output side of the pump 35, increasing line pressure inputted to recycle port 64 on line 51, lifting the flexible diaphragm 65 and increasing the total output of the pump 35 so that a sample of mixed respired gas equal in volume to the amount of additional sample gas released by metering valve 33 is discharged on the second output 52 of the pump 35 for analysis in the $O_2$ and $CO_2$ detectors, respectively.

Figure 5:
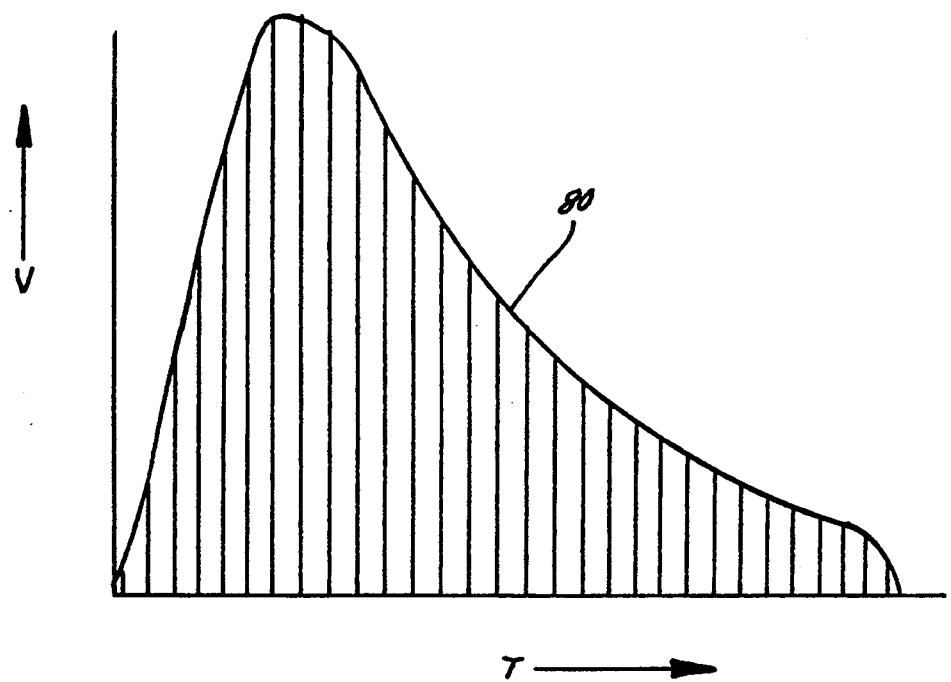
FIG. 5 is a plot of flow versus time for a typical breath.

As heretofore described, the output of the flow detector is proportional to the square of the flow of respired gas through the flow detector. Thus, the microprocessor produces a flow signal representative of the real time flow of respired gas through the flow detector by taking the square root of the output of the differential pressure transducer. With reference to the plot of FIG. 5 of flow signal (V) versus time (T), a typical breath flow curve is illustrated at 80. The area under the curve 80 is representative of the total volume of respired gas and is determined by summing the periodic flow signals, dividing by the number of flow signal samples taken, and multiplying by the elapsed time. This summation technique thus approximates the integral of the curve 80 by summing and operating on the flow signal over the length of the curve 80.

As heretofore described, the flow signal generated by the microprocessor is used to control the output of a pulse generator which has an output with a variable frequency and a variable pulse width. The frequency of the output of the pulse generator is controlled by the microprocessor to be proportional to the flow of respired gas so that a small but volumetrically-proportional sample of respired gas is drawn through the metering valve of the analyzer.

With reference now to FIGS. 6 and 6(a), it is illustrated that derivative augmentation is employed to increase the periodic sampling rate of the microprocessor when the slope of the flow curve 81 is high, and decreasing the sample rate when the slope of the flow curve 81 is low. Further, it is illustrated that the pulse width is varied according to the breath rate determined by the microprocessor. FIG. 6 illustrates a typical flow curve 81 for an individual that is breathing rapidly and deeply. In FIGS. 6 and 6(a) the pulse width is small, approximately 2.5 microseconds, and the processor compares the flow signal at V2 and V1 to determine the time rate of change or slope of the curve 81 and thus determine when the next sample is to be taken. When the slope is rapidly increasing as in segment 83, the sample rate increases. As the slope decreases as in curve segment 82, sampling rate decreases. This increases the resolution or accuracy of the integration of the curve 81 to enhance the calculation of total respired gas and volume.

With reference now to FIGS. 7 and 7(a), it is illustrated that under low flow and breathing rate conditions, such as those illustrated by the curve 87, pulse width is increased to approximately ten microseconds to effectively increase the sample volume and compensate for these low flows. Thus, electronic variable sampling is used to vary the proportional volumetric relationship between the sample and the breath by conducting an analysis of flow and breathing rate. This and derivative augmentation increases the resolution and accuracy of the metabolic rate analyzer of the present invention.

With reference now to FIG. 6(b), it is illustrated that the analog signal 81 of FIG. 6 is converted by the microprocessor and a valve driver circuit (pulse generator), hereinafter described, into a pulse train or digital signal 200 that is frequency-proportional to the amplitude of the waveform 81. This pulse train is applied to the solenoid-actuated metering valve 33. The frequency of the pulse generator has a lower limit of 0.5 Hz and an upper limit of 75 Hz. The upper limit of the pulse generator is determined by the maximum frequency of the solenoid-operated metering valve 33. The metering valve is not operated above a frequency that prevents the valve from closing completely between pulses. During the operation of the analyzer, as the flow signal illustrated at 82 in FIG. 6 increases from zero, the pulse generator provides an initial output of 0.5 Hz. As the flow increases, the frequency of the output of the pulse generator is increased proportionally to the increase in the flow of respired gas. As the flow decreases, the frequency of the pulse generator correspondingly decreases, as illustrated in FIG. 6(b). In this embodiment, full scale for the flow detector is set at 75 Hz, well above the maximum predicted flow rate for an adult human being. Thus, the analog flow signals such as those illustrated at 81 in FIG. 6 (high breath rate and high flow) and at 87 in FIG. 7 (low breath rate and low flow) are converted to digital, frequency-proportional signals that drive the solenoid-operated metering valve 33 to provide a sample of respired gas that is volumetrically-proportional to the detected flow of respired gas.

Figure 10:
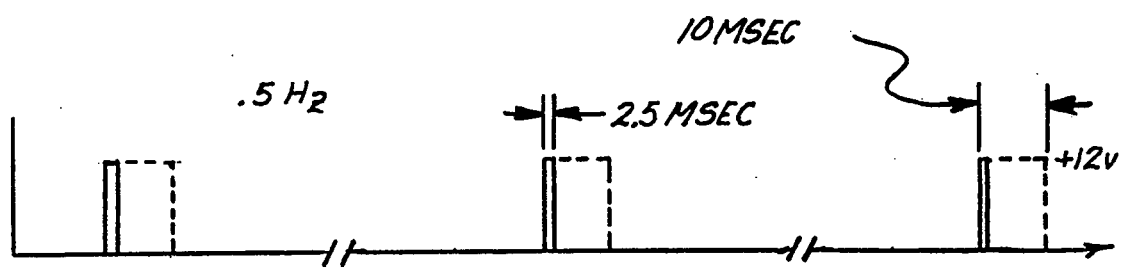
FIG. 10 is a plot of the digital frequency-proportional signal that drives the solenoid-actuated metering valve at 0.5 Hz.
Figure 11:
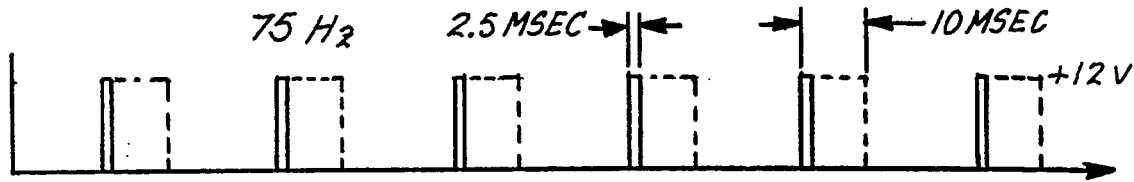
FIG. 11 is a plot of the digital frequency-proportional signal that drives the solenoid-actuated metering valve at 75 Hz.

With reference now to FIGS. 10 and 11, the variable pulse width of the pulse generator is illustrated in further detail. As previously described, a digital, frequency-proportional signal is generated having a low threshold at 0.5 Hz (FIG. 10), and a high threshold at 75 Hz (FIG. 11). In the case where the microprocessor senses high breathing rates, pulse width is set at 2.5 microseconds over the course of any individual breath or an entire processing cycle (20 seconds). However, the processor continuously updates breathing rate, by monitoring the flow signal, and when breath rates are slow, for example when they approach basil rates, the pulse width is proportionally increased to a maximum of 10.0 microseconds. In FIGS. 10 and 11, the solid lines illustrate the pulse train at 0.5 Hz and 75 Hz, respectively, during a high breath rate. The dotted lines in FIGS. 10 and 11 illustrate the widening of the pulses of the pulse train at 0.5 Hz and 75 Hz, respectively, during a period of low breath rate.

Since the pulse width is not varied during the course of an individual breath, the volumetrically-proportional relationship between the sample and the total flow of respired gas is maintained. The importance of the pulse width variation lies in an understanding of the dynamic response of the analyzer. The analyzer establishes a closed loop of mixed respired gas having a constant volume. The washout time of this closed loop must be matched to the flow rate of the subject. High flow rates could washout the closed loop quickly, resulting in slug flow through the system if pulse width was not modulated to reduce sample volume. Similarly, low flow rates could result in a sample volume that is small relative to the volume of the closed loop, which could affect the accuracy of the analyzer in tracking low flows unless pulse width was modulated in increase the sample volume when low flow and breathing rates are sensed.

Figure 8:
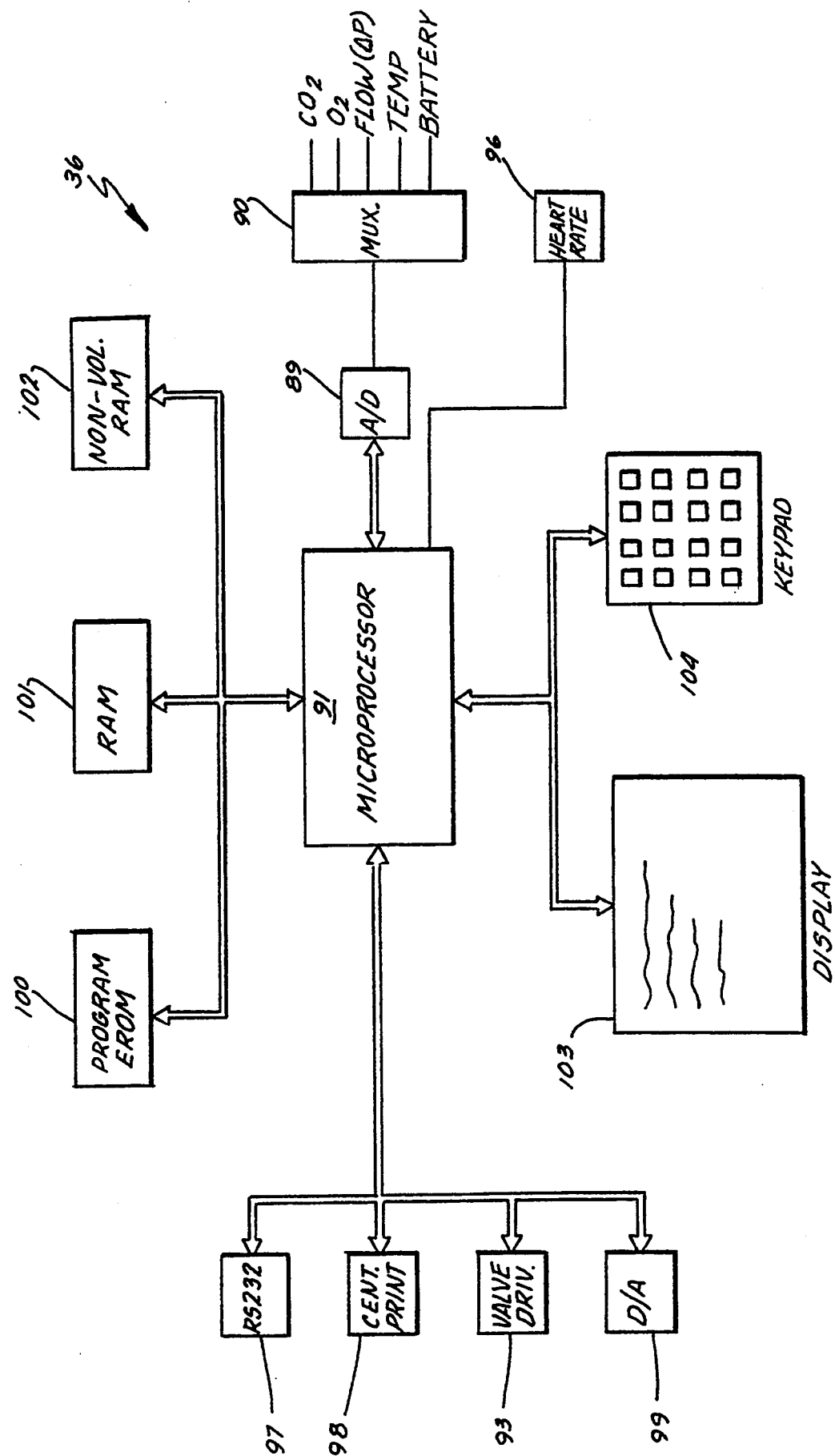
FIG. 8 is a functional diagram of the microprocessor of the metabolic rate analyzer.

The time on and time off signals for the driving circuits and the sampling period are all microprocessor-controlled. With reference now to FIG. 8, a functional diagram of the microprocessor is illustrated at 36. The microprocessor 36 includes an A/D convertor 89 and a multiplexer at 90 for inputting a differential pressure signal, a $CO_2$ signal, an $O_2$ signal, a temperature signal, a battery signal, and auxiliary channels not illustrated in FIG. 8. The A/D converter converts these inputs to digital inputs for a central processor 91. Valve driver circuits at 93 convert the output of the microprocessor 91 into signals that drive all of the solenoid-controlled functions of the analyzer. For example, the microprocessor generates on/off signals for controlling voltage-to-frequency driver generating a series of pulses on line 45 to the actuating coil 94 of solenoid-actuated metering valve 33. Direct digital inputs may also be provided, such as the output of a heart rate monitor 96. An RS232 port at 97 is provided for downloading metabolic rate information directly to a personal computer for further processing and/or storage, and a printer port at 98 is provided for printing extended output of the metabolic rate analyzer. Further, a digital-to-analog (D/A) convertor at 99 may be provided for producing an output signal suitable for varying the intensity of exercise provided by a stationary bicycle or treadmill for maintaining cardiac patients at a constant workload.

A read-only memory is provided at 100. The read-only memory comprises an erasable, programmable read-only memory (EPROM). The operating software for the microprocessor 91 resides in the EPROM 100 and is loaded into the microprocessor 91 during start-up. A random access memory (RAM) is disposed at 101 to provide scratchpad memory for the microprocessor 91 and to store various flags and values on a temporary basis. The RAM is activated and capable of memory storage only when the power is on in the microprocessor 91. A non-volatile memory or RAM is disposed at 102 to store data that must be retained when the power is off. For example, the non-volatile RAM 102 is used to store calibration factors that have been calculated because it is not desirable to conduct a calibration of the unit every time the analyzer is turned on. Other types of data stored in the non-volatile RAM include analyzer serial number, a constant associated with a $CO_2$ calibration window, the subject's weight, etc. Most of the non-volatile RAM is battery-backed RAM; however, some more permanent memory may be provided for important data such as serial number. After start-up, the processor receives real time data from the A/D converter 89 and the multiplexer 90 ($CO_2$, $O_2$, $\Delta P$, Temperature, Battery). The operator can also input data or enter operating instructions through a keypad 104. The real time output of the microprocessor 91 comprises the time on/off signals which control the valve driving circuits 93, output directed to a liquid crystal display (LCD) at 103, output directed to another processor through RS232 port 97, output through a Centronics printer port 98, or output through a D/A converter 99 which controls the work level of an exercise machine such as a stationary bike or treadmill. The data storage devices 101 or 102 can be provided with sufficient capacity to store hours of metabolic data for printout or display later through the display 103 or a printer connected to port 98. The microprocessor 91 is an EPROM-based, dedicated special-purpose microprocessor that includes the timers, ports, etc., that are conventionally associated with such minicomputers.

Figure 9:
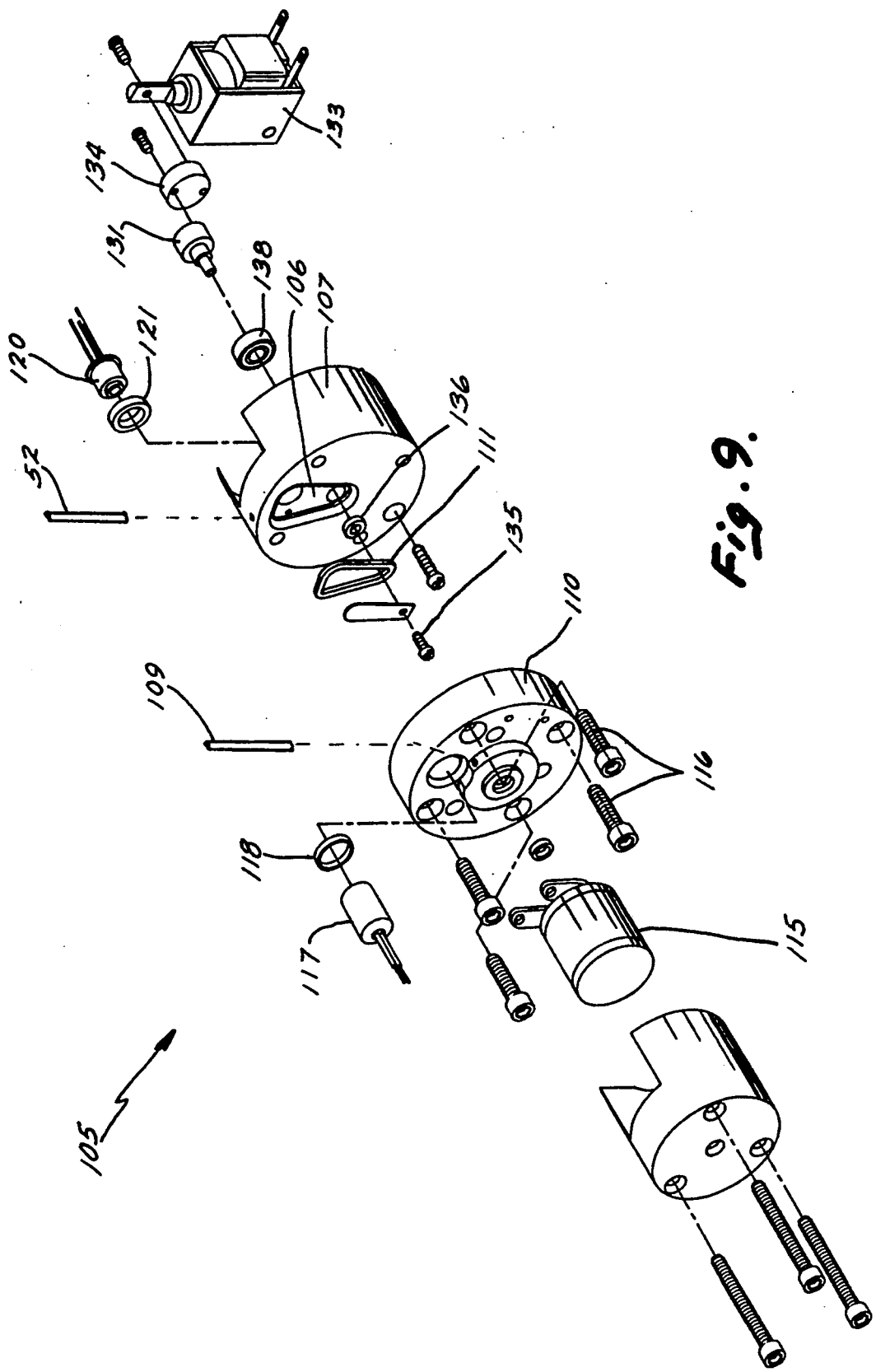
FIG. 9 is an exploded assembly of the $O_2$ and $CO_2$ detector assembly.

With reference now to FIG. 9, the $O_2$ and $CO_2$ detector assembly is generally illustrated at 105. Gas from the second output 52 of the pump 35 is inputted to a gas analysis chamber 106 disposed in a detector body 107. Sample gas is discharged from the unit through an output disposed at 109. The detector body 107 is bifurcated and includes a closure 110, which together with O-ring seal 111, provides a gas-tight sample chamber 106. A galvanic-type $O_2$ detector 115 is disposed in the closure 110. The closure is mounted with a plurality of screws 116 or otherwise suitably secured to the detector body 107. The $O_2$ detector 115 extends into the sample chamber 106 and is a type of detector which reacts directly with atomic oxygen contained in the sample to provide an output that is proportional to the $O_2$ content of the sample gas. A thermopile-type IR detector is disposed at 117 in the closure member 110 surrounded by a seal 118. On the opposite side of the sample cell 106, an IR source is disposed at 120 surrounded by a seal 121. The IR source 120 establishes a beam of infrared energy which extends through the sample chamber 106 and impinges upon the IR detector 117. The IR source 120 is provided with a band-pass filter in the form of a window on the face of the source, which emits a narrow beam of infrared radiation through the sample chamber 106 at a wavelength having known absorption by $CO_2$. Thus, the attenuation of the beam emitted by the IR source 120 reflected in the output of the detector 117 is directly proportional, or has a known relationship, to the $CO_2$ content of the sample contained within the chamber 106.

The $O_2$ detector 115 is spanned by introducing ambient air into the sample chamber 106 by opening the normally-closed solenoid valve 48 illustrated in FIG. 2.

The NDIR detector formed by source 120 and detector 117 is calibrated by provision of a plastic body or calibration window 130, which is pivotally-mounted within the sample chamber 106. The calibration window 130 is formed from a hard plastic having a known $CO_2$ absorption characteristic in the bandwidth of interest for $CO_2$ analysis. The plastic is provided with a predetermined thickness which automatically provides a degree of attenuation comparable to a known $CO_2$ content within the sample chamber 106. Thus, the calibration window 130, during the automatic calibration of the metabolic rate analyzer, is displaced into the optical path between the IR source 120 and IR detector 117 to automatically attenuate the IR beam a predetermined amount which corresponds to a predetermined $CO_2$ content within the sample gas chamber. This provides for automatic calibration of the output of the IR detector 117 without reference to a calibration gas or a reference cell. The calibration window 130 is mounted for reciprocal motion within the gas chamber 106 by fixing the window 130 to the rotatable shaft 131, journaled in the detector body 117. The shaft 131 is connected to a linear solenoid actuator 133 by crank shaft 134. The window 130 is attached to the end of shaft 131 by set screw 135. Thus, when the linear solenoid actuator is pulsed by the microprocessor driver circuit 93 during calibration, the crank shaft 134 displaces shaft 131 and the plastic body 130. The shaft 131 is surrounded by a suitable seal at 136 and a bearing 138.

The above description is exemplary and should be considered that of the preferred embodiment only. Modifications will occur to those skilled in the art when making use of the invention. It is desired to include within the scope of the present invention all such modifications of the invention that come within the proper scope of the appended claims.

The embodiments of the invention in which an exclusive property or privilege is claimed are defined as follows:

1. A metabolic analyzer comprising:
   $CO_2$ detector means for determining a $CO_2$ content of a respired gas;
   $O_2$ detector means for determining an $O_2$ content of the respired gas;
   flow detector means for providing a flow signal representative of the flow of the respired gas;
   flow proportioning valve means for delivering a small, representative and proportional sample of the respired gas having a known volumetrically-proportional relationship with a total volume of the respired gas;
   pump means for drawing the sample of the respired gas from said flow proportioning valve means and delivering the sample to said $CO_2$ and said $O_2$ detector means; and
   processor means for converting said flow signal into a sampling signal that is applied to said flow proportioning valve means to provide a sample of respired gas having a known volumetrically-proportional relationship with the total volume of respired gas, said processor means determining the total volume of respired gas and said processor means correlating total volume, $CO_2$ content and $O_2$ content to provide a measure of metabolic rate.

2. The metabolic analyzer of claim 1 further comprising regulator means for receiving the sample of the respired gas from said flow proportioning valve means and delivering the sample of the respired gas to said pump means.

3. The metabolic analyzer of claim 2 wherein said pump means is provided with a first output and a second output, said first output of said pump means being directed to said regulator means to provide a loop flow of mixed respired gas and said second output being directed to said $CO_2$ and $O_2$ detector means to provide a sample of mixed respired gas.

4. The metabolic analyzer of claim 2 wherein said regulator means comprises a vacuum regulator having a regulator output port maintained at a predetermined vacuum.

5. The metabolic analyzer of claim 4 wherein said regulator means further comprises a regulator input port connected to said flow proportioning valve means for receiving respired gas.

6. The metabolic analyzer of claim 1 wherein said flow detector means comprises an orifice which provides a restriction to the flow of respired gas and a differential pressure transducer for determining the pressure drop across said orifice.

7. The metabolic analyzer of claim 6 wherein said orifice is disposed in a plate and comprises a sharp plate orifice.

8. The metabolic analyzer of claim 7 wherein said differential pressure transducer comprises means for providing a flow signal that is proportional to the square of the flow of respired gas through said sharp plate orifice.

9. The metabolic analyzer of claim 8 wherein said sharp plate orifice is provided with a cross shape.

10. The metabolic analyzer of claim 1 wherein said flow detector means provides a flow signal having a known relationship to the flow of respired gas and said analyzer further comprises pulse generator means for generating said sampling signal, said sampling signal having a variable frequency, the frequency of the said sampling signal being controlled by said processor means and the flow signal so that the frequency of said sampling signal is proportional to the flow of respired gas.

11. The metabolic analyzer of claim 10 wherein said pulse generator means generates said sampling signal with a variable pulse width and said processor means determines the breath rate of an individual being studied by monitoring the flow signal, said processor means controlling the pulse width of said sampling signal, said processor means decreasing the pulse width when breath rate is high and increasing pulse width when breath rate is low to control an effective sample volume of the metabolic analyzer.

12. The metabolic analyzer of claim 10 wherein said flow proportioning valve means further comprises means responsive to the output of said pulse generator means for delivering a volumetrically-proportional sample of respired gas.

13. The metabolic analyzer of claim 12 wherein said flow proportioning valve means comprises a normally-closed, spring-biased, solenoid valve having an actuation coil which overcomes the spring bias when the output of said pulse generator means is applied to said actuation coil, thus opening said flow proportioning valve means to deliver a volumetrically-proportional sample of respired gas.

14. The metabolic analyzer of claim 1 wherein said flow detector means comprises means for providing a flow signal having a known relationship to the flow of respired gas, said processor means comprising means for receiving the flow signal, periodically determining a flow rate value for respired gas and summing said flow rate values to provide a measure of the total volume of respired gas by effectively integrating respired gas flow over time.

15. The metabolic analyzer of claim 14 wherein said flow detector means comprises a sharp plate orifice and a differential pressure transducer, an output of said differential pressure transducer comprising said flow signal, the square root of said flow signal being representative of the flow rate value of respired gas, said processor means periodically sampling said flow signal, taking the square root of said flow signal to form a flow rate value, summing said flow rate values, dividing by the number of flow rate values formed, and multiplying by the elapsed time to provide a measure of the total volume of respired gas by digital integration.

16. The metabolic analyzer of claim 1 wherein said flow detector means comprises means for providing a flow signal having a known relationship to the flow of respired gas, said processor means comprises means for receiving and periodically sampling the flow signal; said processor means periodically determining a flow rate value and comparing flow rate values to determine a time rate of change (slope) for said flow rate values; said processor means increasing a periodic sample rate when the slope is increasing and decreasing the periodic sample rate when the slope is decreasing to provide a derivative augmentation of the sample rate of the metabolic analyzer.

17. The metabolic analyzer of claim 16 wherein said flow detector means comprises a sharp plate orifice and a differential pressure transducer, an output of said pressure transducer comprising said flow signal, the square root of said flow signal comprising said flow rate value, said processor means periodically determining the square root of said flow signal and the slope of the square root of said flow signal.

18. The metabolic analyzer of claim 1 wherein said $O_2$ detector means comprises a galvanic cell.

19. The metabolic analyzer of claim 1 wherein said $CO_2$ detector means comprises a non-dispersive infrared (NDIR) gas analyzer.

20. The metabolic analyzer of claim 19 wherein said NDIR gas analyzer further comprises:
an infrared (IR) source of energy in a bandwidth having a known absorption by $CO_2$;
a sample cell through which the respired gas passes;
an IR detector;
said IR source being disposed on one side of said sample cell and said IR detector being disposed on another side of said sample cell for measuring the absorption of IR due to the $CO_2$ content of the respired gas and to provide a signal representative of the $CO_2$ content of the respired gas.

21. The metabolic analyzer of claim 20 wherein said NDIR gas analyzer further comprises a body having a known absorption for IR energy that corresponds to a predetermined $CO_2$ content in a gas being studied; and a mechanical transport for reciprocally placing said body between said source and said detector to calibrate said NDIR analyzer.

22. A metabolic analyzer comprising:
$CO_2$ detector means for determining a $CO_2$ content of a respired gas;
$O_2$ detector means for determining an $O_2$ content of the respired gas;

flow detector means for providing a flow signal representative of the flow of the respired gas;

flow proportioning valve means for delivering a sample of the respired gas having a known volumetrically-proportional relationship with a total volume of the respired gas;

pump means for drawing the sample of the respired gas from said flow proportioning valve means and delivering the sample to said $CO_2$ and said $O_2$ detector means, said pump means having a pump inlet and a pump outlet;

vacuum regulator means for receiving the sample of the respired gas from said flow proportioning valve means and delivering the sample to said pump means, said vacuum regulator means having a regulator input port connected to said flow proportioning valve means for receiving the sample, a regulator output port maintained at a predetermined vacuum, and a regulator recycle port, said pump inlet being connected to said regulator output port and said pump outlet being connected to said regulator recycle port to provide a loop for mixing respired gas; and processor means for converting said flow signal into a sampling signal that is applied to said flow proportioning valve means to provide a sample of respired gas having a known volumetrically-proportional relationship with the total volume of respired gas, said processor means determining the total volume of respired gas, and said processor means correlating total volume, $CO_2$ content and $O_2$ content to provide a measure of metabolic rate.

23. The metabolic analyzer of claim 22 wherein said pump outlet is also connected to said $CO_2$ detector means and said $O_2$ detector means to provide a sample of mixed respired gas to said $CO_2$ and $O_2$ detector means when said flow proportioning valve means releases respired gas to said vacuum regulator means.

24. The metabolic analyzer of claim 23 further comprising a calibration valve connected to said regulator input port for introducing ambient air to span and calibrate said $CO_2$ and $O_2$ means.

25. A metabolic analyzer comprising:

$CO_2$ detector means for determining an $CO_2$ content of a respired gas;

$O_2$ detector means for determining an $O_2$ content of the respired gas;

flow detector means for providing a flow signal representative of the flow of the respired gas;

flow proportioning valve means for delivering a sample of the respired gas having a known volumetrically-proportional relationship with a total volume of the respired gas;

pump means for drawing the sample of the respired gas from said flow proportioning valve means and delivering the sample to said $CO_2$ and $O_2$ detector means, said pump means having a pump inlet and a pump outlet;

vacuum regulator means for receiving the sample of the respired gas from said flow proportioning valve means and delivering the sample to said pump means, said vacuum regulator means comprising:

a regulator body defining a gas chamber;

a regulator input port for receiving respired gas from said flow proportioning valve means;

a regulator output port for delivering respired gas to said pump inlet;

a flexible diaphragm disposed between said regulator input port and said regulator output port, said diaphragm dividing said gas chamber into an input side and an output side in fluid communication with said regulator input port and said regulator output port, respectively;

a regulator metering port disposed in said diaphragm for establishing a fluid communication between said input side and said output side of said gas chamber;

a regulator recycle port in fluid communication with said regulator output side;

a regulator transfer port disposed in said output side of said gas chamber for supplying respired gas to said regulator output port, said diaphragm being spring-biased against said transfer port to keep said transfer port normally closed except for said metering port which extends therethrough;

said pump inlet being connected to said regulator output port and said pump outlet being connected to said regulator recycle port to form a loop for mixing respired gas; and said pump outlet being connected to said $CO_2$ detector means and said $O_2$ detector means to provide a sample of mixed respired gas to said $CO_2$ and $O_2$ means when said flow proportioning valve means introduces a volume of respired gas to said input side of said gas chamber of said vacuum regulator means; and processor means for converting said flow signal into a sampling signal that is applied to said flow proportioning valve means to provide a sample of respired gas having a known volumetrically-proportional relationship with the total volume of respired gas, said processor means determining the total volume of respired gas, and said processor means correlating total volume, $CO_2$ content and $O_2$ content to provide a measure of metabolic rate.

26. A metabolic rate analyzer comprising:

$CO_2$ detector means for determining a $CO_2$ content of a respired gas;

$O_2$ detector means for determining an $O_2$ content of the respired gas;

a flow restriction through which the respired as is directed;

differential pressure detector means connected to said flow restriction for providing a differential pressure signal representative off the flow of respired gas through said flow restriction;

solenoid-actuated flow proportioning valve means adapted to be connected to a source of respired gas for delivering a small, representative and volumetrically-proportional sample of respired gas;

vacuum regulator means for receiving the sample;

pump means for drawing the sample from said vacuum regulator means and delivering the sample to said $CO_2$ and $O_2$ detector means; and processor means for converting said differential pressure signal into a flow signal that is representative of a volumetric flow of respired gas that established said differential pressure signal, said processor means using said flow signal to modulate electrical power applied to said solenoid-actuated flow proportioning valve means to provide a sample of respired gas having a known volumetrically-proportional relationship with the total volume of respired gas, said processor means determining the total volume of respired gas and correlating total volume, $CO_2$ content and $O_2$ content to provide a measure of metabolic rate.

27. A metabolic rate analyzer comprising:

$CO_2$ detector means for providing a $CO_2$ signal representative of the $CO_2$ content of a respired gas;

$O_2$ detector means for providing an $O_2$ signal representative of the $O_2$ content of the respired gas;

a sharp plate orifice through which the respired gas is directed;

differential pressure transducer means for providing a pressure signal representative of the difference in pressure of the respired gas on opposite sides of said orifice;

solenoid-actuated flow proportioning valve means adapted to be connected to a source of respired gas for delivering a small, representative volumetrically-proportional sample of respired gas;

vacuum regulator means for receiving the sample of respired gas;

pump means for drawing the sample of respired gas from said vacuum regulator means, said pump means being provided with a first output and a second output;

said first output of said pump means being directed to said vacuum regulator means to provide a loop flow of mixed respired gas;

said second output of said pump means being directed to said $CO_2$ detector means and said $O_2$ detector means for delivering mixed respired gas thereto;

processor means for periodically sampling said pressure signal and taking the square root of said pressure signal to provide a flow signal representative of the flow of respired gas;

pulse generator means having a variable frequency and variable pulse width output controlled by said processor means and said flow signal, the frequency of the output of said pulse generator means increasing with an increase in the flow signal and decreasing with a decrease in the flow signal, the output of said pulse generator means being applied to said solenoid-actuated flow proportioning valve means;

said processor means summing said flow signals, dividing by the number of flow signals taken, and multiplying by elapsed time to provide a measure of the total volume of respired gas, thus effectively integrating said flow signal;

said processor means monitoring said flow signal to determine a breath rate and for increasing the pulse width of the output of said pulse generator means when breath rate is low and for decreasing pulse width when breath rate is high, thus controlling an effective sample volume of the analyzer;

said processor means having a variable period for sampling said flow signal, said processor means determining a slope of said flow signal for decreasing said period when the slope is increasing and increasing said period when the slope is decreasing, thus effecting derivative augmentation of said variable period for sampling;

said processor means correlating said measure of the total volume of respired gas, said $CO_2$ signal and said $O_2$ signal to provide a measure of metabolic rate.

28. A metabolic analyzer comprising:

$CO_2$ detector means for determining a $CO_2$ content of a respired gas, said $CO_2$ detector means comprising a non-dispersive infrared (NDIR) gas analyzer having an infrared (IR) source and a means for calibrating said NDIR analyzer comprising a means for attenuating said IR source;

$O_2$ detector means for determining an $O_2$ content of the respired gas;

flow detector means for providing a flow signal representative of the flow of the respired gas;

flow proportioning valve means for delivering a small, representative and proportional sample of the respired gas having a known volumetrically-proportional relationship with a total volume of the respired gas;

pump means for drawing the sample of the respired gas from said flow proportioning valve means and delivering the sample to said $CO_2$ and said $O_2$ detector means; and processor means for converting said flow signal into a sampling signal that is applied to said flow proportioning valve means to provide a sample of respired gas having a known volumetrically-proportional relationship with the total volume of respired gas, said processor means determining the total volume of respired gas and said processor means correlating total volume, $CO_2$ content and $O_2$ content to provide a measure of metabolic rate.

29. A metabolic analyzer comprising:

$CO_2$ detector means for determining a $CO_2$ content of a respired gas;

$O_2$ detector means for determining an $O_2$ content of the respired gas;

flow detector means for providing a flow signal representative of the flow of the respired gas;

flow proportioning valve means for delivering a small, representative and proportional sample of the respired gas having a known volumetrically-proportional relationship with a total volume of the respired gas;

pump means for drawing the sample of the respired gas from said flow proportioning valve means, said pump means being provided with an inlet, a first output and a second output, said first output being connected back to said inlet to provide a recirculation loop of mixed respired gas and said second output being connected to said $CO_2$ and $O_2$ detector means to provide a sample of mixed respired gas; and processor means for converting said flow signal into a sampling signal that is applied to said flow proportioning valve means to provide a sample of respired gas having a known volumetrically-proportional relationship with the total volume of respired gas, said processor means determining the total volume of respired gas and said processor means correlating total volume, $CO_2$ content and $O_2$ content to provide a measure of metabolic rate.

30. A metabolic analyzer comprising:

$CO_2$ detector means for determining a $CO_2$ content of a respired gas;

$O_2$ detector means for determining an $O_2$ content of the respired gas;

flow detector means for providing a flow signal representative of the flow of the respired gas;

flow proportioning valve means for delivering a small, representative and proportional sample of the respired gas having a known volumetrically-proportional relationship with a total volume of the respired gas;

pump means for drawing the sample of the respired gas from said flow proportioning valve means and delivering the sample to said $CO_2$ and said $O_2$ detector means; and processor means for converting said flow signal into a sampling signal that is applied to said flow proportioning valve means to provide a sample of respired gas having a known volumetrically-proportional relationship with the total volume of respired gas, said processor means having a sample period for sampling said flow signal, said processor means determining the slope of said flow signal for decreasing said period when the slope is increasing and increasing said period when the slope is decreasing to provide derivative augmentation of said sample period, said processor means determining the total volume of respired gas and said processor means correlating total volume, $CO_2$ content and $O_2$ content to provide a measure of metabolic rate.

31. A metabolic analyzer comprising:

$CO_2$ detector means for determining a $CO_2$ content of a respired gas;

$O_2$ detector means for determining an $O_2$ content of the respired gas;

flow detector means for providing a flow signal representative of the flow of the respired gas;

flow proportioning valve means for delivering a small, representative and proportional sample of the respired gas having a known volumetrically-proportional relationship with a total volume of the respired gas;

pump means for drawing the sample of the respired gas from said flow proportioning valve means and delivering the sample to said $CO_2$ and said $O_2$ detector means; and processor means for converting said flow signal into a sampling signal that is applied to said flow proportioning valve means to provide a sample of respired gas having a known volumetrically-proportional relationship with the total volume of respired gas, said sampling signal comprising a series of digital pulses having a pulse width, said processor means monitoring said flow signal to determine a breath rate for increasing said pulse width when breath rate is low and decreasing said pulse width when breath rate is high for providing a variable sample volume, said processor means determining the total volume of respired gas and said processor means correlating total volume, $CO_2$ content and $O_2$ content to provide a measure of metabolic rate.

32. A metabolic analyzer comprising:

$CO_2$ detector means for determining a $CO_2$ content of a respired gas;

$O_2$ detector means for determining an $O_2$ content of the respired gas;

flow detector means for providing a flow signal representative of the flow of the respired gas;

flow proportioning valve means for delivering a small, representative and proportional sample of the respired gas having a known volumetrically-proportional relationship with a total volume of the respired gas;

pump means for drawing the sample of the respired gas from said flow proportioning valve means and delivering the sample to said $CO_2$ and said $O_2$ detector means; and processor means for converting said flow signal into a sampling signal that is applied to said flow proportioning valve means to provide a sample of respired gas having a known volumetrically-proportional relationship with the total volume of respired gas, said sampling signal comprising a series of digital pulses having a frequency, said processor means monitoring said flow signal for increasing said frequency when said flow signal increases and decreasing said frequency when said flow signal decreases for providing a proportional sample, said processor means determining the total volume of respired gas and said processor means correlating total volume, $CO_2$ content and $O_2$ content to provide a measure of metabolic rate.

* * * * *